United States Patent [19]

Shulman et al.

[11] 4,004,006
[45] Jan. 18, 1977

[54] CONTRACEPTIVE AND ANTIVENEREAL AGENTS

[76] Inventors: Albert Shulman; Glenda Maud Shulman, both of Flat 2, 1 Muntz St., North Caulfield, Australia, 3161

[22] Filed: Nov. 12, 1974

[21] Appl. No.: 523,172

[30] Foreign Application Priority Data

Nov. 12, 1973 Australia ............................ 5608/73

[52] U.S. Cl. ................ 424/245; 424/16; 424/47
[51] Int. Cl.² ...................................... A61K 31/555
[58] Field of Search ........................... 424/294, 245

[56] References Cited

FOREIGN PATENTS OR APPLICATIONS

| 251,506 | 1/1961 | Australia | 424/245 |
| 251,582 | 1/1961 | Australia | 424/245 |
| 251,598 | 1/1961 | Australia | 424/245 |
| 251,889 | 1/1960 | Australia | 424/245 |

OTHER PUBLICATIONS

Goodwin et al., Chem. Abs., 1972, vol. 76 p. 41405y.
Kawasciades et al., Chem. Abs., 1970, vol. 72, p. 6676h.
Rehorek et al., Chem. Abs, 1974, vol. 80, p. 89257m.
Rehorek et al., B. Anorg. Allg. Chemie, 1973 Bd. 402 Heff 1 pp. 58–66.
James et al. J. Chem. Soc. 1961 pp. 4630–4637.
Irving J. Chem. Soc. 1962, pp. 5222–5237.

*Primary Examiner*—Dale R. Ore
*Attorney, Agent, or Firm*—Dennison, Dennison, Meserole & Pollack

[57] ABSTRACT

This invention discloses the use of chelates formed from transition metals and 1,10-phenanthroline or 2,2'-bipyridine as contraceptives adapted for intravaginal use which also give high protection against venereal disease.

Specifically high activity is shown for the copper (I) and copper (II) chelates of the bases, particularly when these are substituted with a number of substituents.

28 Claims, No Drawings

CONTRACEPTIVE AND ANTIVENEREAL AGENTS

This invention relates to the use of certain metal chelates as contraceptive antivenereal agents and particularly to certain fully co-ordinated chelates derived from transition metal ions and 1,10-phenanthroline and 2,2′-bipyridine bases and their substituted derivatives. Chelates of the general classes to which this invention relates have previously been described in the specifications of Australian Pat. Nos. 251,506; 251,582; 251,889 and 251,598. Especially in Australian Pat. No. 251,506, the specification refers to certain substituted 1,10-phenanthroline and substituted 2,2′-bipyridine bases; and to certain mono N-alkylated derivatives of such bases; and to certain metal complexes with homogeneous organic ligands comprising two or three molecules of such bases. In this regard, the numbering of 1,10-phenanthroline hereinafter is in agreement with ring No. 1954 page 264 of "The Ring Index" A. M. Patterson and L. I. Capell, Monograph Series, published 1940 by Rheinhold Publishing Corporation and the numbering of 2,2′-bipyridine hereinafter is as conventionally accepted; whilst the term 'metal chelates' or 'metal complexes' is to be understood as designating those stable compounds arising from the ability of metals or metal ions to combine with definite numbers of neutral molecules, ions or groups (vide:Kirk Othmer "Encyclopedia of Chemical Technology" Vol IV page 379 published 1949 by Interscience); and the term 'ligand' or 'ligand group' is to be understood as designating functional or co-ordinating groups which have one or more pairs of electrons available for the formation of co-ordinate bonds (vide:Kirk Othmer "Encyclopedia of Chemical Technology" Vol IV page 382 published 1949 by Interscience).

As discussed in the specification of Australian Pat. No. 251,506, fully co-ordinated chelates derived from divalent transition metals ions and 1,10-phenanthroline bases are known to have diverse biological actions such as lethality to a variety of microorganisms pathogenic to man, domestic animals and plants.

While such metal chelates generally block the neuromuscular junction when administered parenterally to animals, selected chelates have been used clinically, and, as far as can be seen, with complete safety for the prevention and treatment of a variety of topical infections of skin, subcutaneous tissues and mucous membranes including ear, nose, eye, vagina and traumatic or surgical wounds. Bis(3,4,7,8-tetramethyl-1,10-phenanthroline)copper(II) diacetate has been especially useful in the treatment of intractable cases of monilial and trichomonal vaginitis and monilial nailfold infection, while tris(3,4,7,8-tetramethyl-1,10-phenanthroline)nickel(II)sulphate has been very effective for the prevention of staphylococcal infection in the newborn and patients undergoing surgery, and in eliminating established infection due to *Staphylococcus aureus* and other Gram-positive and certain Gram-negative bacteria.

It is an object of the invention to use certain of these known chelates both as a clinical contraceptive in man and lower animal species and, in an ancillary role, as an antivenereal agent in man.

The invention includes in its broadest aspect as a contraceptive agent in a suitable carrier metal chelates of the structural formulae:

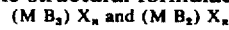

wherein M represents a metal selected from ferrous (iron(II)), zinc(II), manganous (manganese(II)), cobaltous (cobalt(II)), cobaltic (cobalt(III)), cuprous(copper(I)), cupric(copper(II)), nickelous(nickel(II)), chromous (chromium(II)), chromic(chromium (III)), cadmium(II), ruthenous(ruthenium(II)), osmous(osmium(II)), platinous(platinum(II)), palladous(palladium(II)), rhodic(rhodium (III)), and iridous(iridium- (III)), wherein B represents a ligand provided by a base consisting of 1,10-phenanthroline, 2,2′-bipyridine or their substituted derivatives, if substituted the 1,10-phenanthroline base having substituents and mixtures of substituents selected from alkyl, thioalkyl aryl, alicyclic, heterocyclic, nitro and chloro in one to eight of the 2-, 3-, 4-, 5-, 6-, 7-, 8-, and 9-, positions and, if substituted the 2,2′-bipyridine base having substituents and mixtures of substituents selected from alkyl, thioalkyl aryl, alicyclic, heterocyclic, nitro and chloro in one to six of the 4-, 5-, 6-, 4′-, 5′-, and 6′- positions, in the case of 1,10-phenanthroline the substitution being in one to eight of the specified positions with the alkyl and thioalkyl group and in one or two of the specified positions with the nitro, chloro, aryl, alicyclic and heterocyclic groups, each alkyl and thioalkyl substituent comprising one to sixteen carbon atoms, the total of all carbon atoms in such substituents not exceeding 16, and where disubstitution involves the 3-, 4-, and 7-, 8-, positions either pairs of carbon atoms may form part of 5- membered and 6- membered cycloalkane ring systems and such aryl, alicyclic and heterocyclic mono- and di-substituents totalling from four to sixteen carbon atoms, and in the case of the 2,2′-bipyridine there being substitution in one to six of the specified positions with the alkyl and thioalkyl groups, and mono-substitution and di-substitution in the 4- and 4′- and 5-, and 5′- positions with the nitro, chloro, aryl, alicyclic and heterocyclic groups, each alkyl and thioalkyl, substituent comprising one to sixteen carbon atoms, the total of all carbon atoms in such substituents not exceeding sixteen, and such aryl, alicyclic and heterocyclic substituents totalling from four to sixteen carbon atoms; wherein X represents the anion of inorganic and organic acids; and wherein *n* represents an integer determined by the oxidation state of the metal. Normally, the liquid B would have six or less substituents in the case of 1,10-phenanthroline bases and four or less in the case of 2,2′-bipyridine bases.

The invention also relates to a contraceptive (in man and lower animals) and antivenereal agent (in man), constituted as above, present in a suitable carrier.

Suitable carriers are those of the type generally known in the art as being satisfactory for intravaginal use such as aerosol foams, jellies, creams, foam tablets and pessaries (suppositories).

In order that the invention may be more fully described, we have determined the speed with which various metal chelates differing in the transition metal ion or ligand immobilize human spermatozoa and kill the types of microorganisms, *Neisseria gonorrhoea* and *Treponema pallidum*, which are responsible for the production of clinical gonorrhoeae and syphilis respectively. Also we have examined the effects of certain metal ions and ligands on these three test systems and shown that it is most likely the chelate cation as a whole rather than its constituent metal ion or ligand which is the predominantly active species. We have also shown for Cu(II) chelates that the inactivation times for human spermatozoa and *N. gonorrhoea* generally decreased with an increase in the number of alkyl substituent groups present in the chelate. The results are shown in Tables 1 and 2.

Speed of action of selected test substances on human spermatozoa

Samples of human semen containing a minimum sperm count of 60 ×10$^6$ /ml with at least 60% motility were allowed to stand for some 20 minutes after collection. One drop of the test substance (15 or 7.5mM) dissolved in isotonic sodium chloride or sodium acetate was mixed with one drop of semen on a microscope slide giving a final concentration of 7.5 or 3.8mM. The time in minutes required for complete sperm immobilization by the test substance at 22°–23° C was determined microscopically at 400 magnifications. Generally, human spermatozoa in semen mixed only with isotonic sodium chloride or sodium acetate showed good motility on the slide for at least 40 minutes.

The compounds used were all fully co-ordinated divalent transition metal chelate cations of 1,10-phenanthroline or diversely substituted 1,10-phenanthroline or 2,2'-bipyridine bases. The Cu(II), Cd(II), Zn(II) and the Mn(II) chelates generally contained two ligands while the remainder contained three. The anion of the Fe(II) and Ni(II) chelates was sulphate while in all other cases it was acetate.

In tests with the metal ions we used the diacetates of Cu(II), Zn(II), Mn(II), and Co(II) and the sulphates of Fe(II) and Ni(II) while the ligands 1,10 -phenanthroline and 3,4,7,8-tetramethyl-1,10-phenanthroline were tested as the hydrochlorides.

Representative times (min) for the complete immobilization of spermatozoa by metal chelate test substances (7.5mM) are shown in Table 1.

The immobilizing action of the Cu(II) chelate of 3,4,7,8-tetramethyl-1,10-phenanthroline on human spermatozoa was irreversible and the average time taken for immobilization was dependent on the chelate concentration, as follows:

| 0.85mM | 1.9mM | 3.8mM | 7.5 to 15mM |
|--------|-------|-------|-------------|
| 11 min | 5 min | 2 min | <1–2 min    |

The Cu(II) chelate was even more active against dog spermatozoa. With the corresponding nickel(II) chelate (7.5 to 15mM) there was complete loss of human sperm motility in 20–40 minutes.

Although not shown in Table 1, human spermatozoa were also rapidly immobilized by the Cu(II) chelates (as diacetates) of 3,4-(CH$_3$)$_2$-phen, 4,5-(CH$_3$)$_2$-phen, 5,6-(CH$_3$)$_2$-phen, 3,4,7-(CH$_3$)$_3$-phen, 3,4,8-(CH$_3$)$_3$-phen, 3,4,5,6-(CH$_3$)$_4$-phen, 3,4,7,8-(CH$_3$)$_4$-phen, and 3,5,6,8-(CH$_3$)$_4$-phen(3.8mM), representative times for complete loss of motility being 3-4, 3-6, 2-3, 3-6, 2-3, 3-6, 2 and 2 minutes respectively.

Speed of action of selected test substances on human spermatozoa, *N. gonorrhoea* and *Trep. pallidum*

The method of preparation of the human spermatozoa and the type of test carried out were identical to those described previously, the chelate concentration was 7.5mM.

The studies with the two microorganisms were carried out as follows:

*Neisseria gonorrhoea:*

A suspension of *N. gonorrhoea* in 10% serum broth was prepared from a 48 hour culture on lysed-blood agar and used to inoculate (10%) serum broth containing the test substance (100 μM) added 1:40 from an

TABLE 1

| Ligand | Transition Metal Ion. | | | | | | |
|--------|--------|--------|--------|--------|--------|--------|--------|
|        | Cu(II) | Cd(II) | Zn(II) | Mn(II) | Co(II) | Fe(II) | Ni(II) |
| 1,10-phenanthroline (phen) | 15 | 40 | > 40 | > 40 | > 40 | > 40 | > 40 |
| 5-Cl-phen | 6 | > 40 | > 40 | 40 | 23 | > 40 | > 40 |
| 5-NO$_2$-phen | > 40 | > 40 | > 40 | — | > 40 | > 40 | > 40 |
| 5-(C$_6$H$_5$)-phen | 2.5 | 15 | — | 30 | 30 | > 40 | 20 |
| 5-(CH$_3$)-phen | 4 | 30 | > 40 | > 40 | > 40 | > 40 | > 40 |
| 3,8-(CH$_3$)$_2$-phen | 2.5 | 15 | > 40 | > 40 | 35 | > 40 | > 40 |
| 4,7-(CH$_3$)$_2$-phen | 2.5 | 40 | > 40 | > 40 | 40 | > 40 | > 40 |
| 3,4,7,8-(CH$_3$)$_4$-phen | 2 | 13 | 22 | 28 | 18 | 38 | > 40 |
| 3,4,5,6,7,8-(CH$_3$)$_6$-phen | 1 | 1 | 1 | 4 | — | 25 | 8 |
| 3,8-(CH$_3$)$_2$-4,7-(C$_2$H$_5$)$_2$-phen | 1.5 | — | — | 3* | 1.5 | 4 | 2* |
| 3,8-(C$_2$H$_5$)$_2$-5,6-(CH$_3$)$_2$-phen | 1 | — | — | — | — | — | 2.5 |
| 3,8-(C$_4$H$_9$)$_2$-5,6-(CH$_3$)$_2$-phen | — | — | 0.5* | — | 0.5 | 0.5 | 0.5 |
| 4,4'-(CH$_3$)$_2$-5,5'-(C$_2$H$_5$)$_2$-2,2'-bipyridine | 2 | — | — | — | 5 | 20 | — |

*tested at 3.8mM owing to limited solubility.

It can be seen that the immobilization times varied greatly and depended on both the nature of the metal ion and ligand present in the chelate. Generally, speed of immobilization was most rapid for the Cu(II) chelates and for compounds containing at least four alkyl substituent groups in the 1,10-phenanthroline or 2,2'-bipyridine ring.

The transition metal ions Cu(II), Cd(II), Zn(II), Mn(II), Co(II), Fe(II) and Ni(II) (7.5mM) and the ligands 1,10-phenanthroline and 3,4,7,8-tetramethyl-1,10-phenanthroline (7.5mM) were all slowly acting. In each case, the time required for complete loss of motility of the spermatozoa was in excess of 40 minutes. For the Cu(II) and Ni(II) chelates of 3,4,7, 8-tetramethyl-1,10-phenanthroline, the concentration used in this test approximated to that which has been administered clinically in a vaginal pessary.

aqueous stock solution. The incubating medium was mixed and sampled by Pasteur pipette within 20–30 sec. into heart-infusion broth to dilute (1:100) the test compound to a sub-inhibitory concentration. One drop (approximately 30 μl) of the diluent was spotted onto a well-dried, lysed-blood agar plate. Similar samplings were made at 1,2.5,5,10,20 and 30 min. after inoculation. This incubation procedure was repeated at the end of each series of tests using distilled water instead of test compound to confirm the viability of the organism. The whole procedure was carried out at 35°–37° C and the plates were incubated in a humid CO$_2$ atmosphere in a Fildes jar at 36° C for 48 hours. The time of kill was taken as the shortest sampling time at which no growth was obtained.

*Treponema pallidum:*

An aqueous solution of the test substance was added (1:40) to a 3-day culture of Reiter's strain of *Trep. pallidum* grown in sterility test medium (Baltimore Biological Laboratory) containing 0.1% agar (Davis) and 10% heat-inactivated horse serum to give a final concentration of 100 μM. After mixing, the incubating medium was sampled as a 10% inoculum into fresh medium 20sec., 1,2.5,5,10,20 and 30 min after the addition of chelate. The procedure was carried out at 35°-37° C and the samples incubated at 36° C for 3 days. The time of kill was taken as the shortest sampling time at which no growth was obtained.

The test metal chelates and their speed of action on the three test systems are shown in Table 2.

strongly precipitate constitutents of the semen almost immediately following their mixing on the microscope slide. Such precipitation is accompanied by the complete immobilization or marked slowing in forward movement of all observable spermatozoa. Consequently, allowing additionally for the likely impedence to motility provided by the carrier, the time for immobilization of human spermatozoa in the vagina by an active chelate should be substantially less than that shown in Tables 1 and 2 and should be such as to produce clinically effective contraceptive action.

At the same time, provided an adequate concentration of chelate reaches the microorganisms in the vagina, the rapid kill of *N. gonorrhoea* and *Trep. pallidum*

TABLE 2

| Chelate cation** | Time (min) for action against: | | |
|---|---|---|---|
| | Spermatozoa | N. gonorrhoeae | Trep. pallidum |
| [Cu(phen*)$_2$] | 15 | 5 | 5–10 |
| [Cu(5-(C$_6$H$_5$)-phen)$_2$] | 2.5 | 2.5 | 5 |
| [Cu(5-(CH$_3$)-phen)$_2$] | 4 | 2.5 | 2.5–5 |
| [Cu(2,9-(CH$_3$)$_2$-phen)$_2$] | 0.5–1 | 2.5 | — |
| [Cu(3,8-(CH$_3$)$_2$-phen)$_2$] | 2.5 | 1 | 5–10 |
| [Cu(4,7-(CH$_3$)$_2$-phen)$_2$] | 2.5 | 2.5 | 2.5–5 |
| [Cu(3,4,7,8-(CH$_3$)$_4$-phen)$_2$] | 2 | 1 | 2.5–5 |
| [Cd(3,4,7,8-(CH$_3$)$_4$-phen)$_2$] | 20 | 10–20 | > 30 |
| [Zn(3,4,7,8-(CH$_3$)$_4$-phen)$_2$] | 25 | 20–30 | > 30 |
| [Mn(3,4,7,8-(CH$_3$)$_4$-phen)$_2$] | 28 | 10–20 | > 30 |
| [Co(3,4,7,8-(CH$_3$)$_4$-phen)$_2$] | 15 | > 30 | > 30 |
| [Fe(3,4,7,8-(CH$_3$)$_4$-phen)$_3$] | > 30 | 20 | > 30 |
| [Ni(3,4,7,8-(CH$_3$)$_4$-phen)$_3$] | > 30 | > 30 | > 30 |
| [Cu(3,4,5,6,7,8-(CH$_3$)$_6$-phen)$_2$] | 1 | 1 | 2.5–5 |
| [Cu(3,8-(CH$_3$)$_2$-4,7-(C$_2$H$_5$)$_2$-phen)$_2$] | 1–1.5 | 1 | 2.5–5 |
| [Co(3,8-(CH$_3$)$_2$-4,7-(C$_2$H$_5$)$_2$-phen)$_3$] | 1–1.5 | 10 | > 30 |
| [Cu(3,8-(C$_2$H$_5$)$_2$-5,6-(CH$_3$)$_2$-phen)$_2$] | 0.5–1.5 | 1 | 2.5–5 |
| [Ni(3,8-(C$_2$H$_5$)$_2$-5,6-(CH$_3$)$_2$-phen)$_3$] | 2.5 | 10–20 | > 30 |
| [Zn(3,8-(C$_4$H$_9$)$_2$-5,6-(CH$_3$)$_2$)-phen)$_2$] | 0.5–1 | 5–10 | 20 |
| [Ni(3,8-(C$_4$H$_9$)$_2$-5,6-(CH$_3$)$_2$-phen)$_3$] | 0.5–1 | > 30 | 5–10 |
| [Cu(4,4'-(CH$_3$)$_2$-5,5'-(C$_2$H$_5$)$_2$-bipy°)$_2$] | 2.5 | 5–10 | 10 |

**The anion of the Fe(II) and Ni(II) chelates was sulphate while in all other cases it was acetate.
*1,10-phenanthroline
°2,2'-bipyridine.

Generally, it may be seen that speed of inactivation of the spermatozoa and both microorganisms was most rapid for the Cu(II) chelates. With the exception of *Trep. pallidum*, this was especially so for compounds containing at least four alkyl substituent groups in the 1,10-phenanthroline ring. The Zn(II) chelate of 3,8-dibutyl-5,6-dimethyl-1,10-phenanthroline and the Cu(II) chelate of 4,4'-dimethyl-5,5'-diethyl-2,2'-bipyridine also showed reasonably rapid activity on the three test systems.

The transition metal ions Cu(II), Cd(II), Zn(II), Mn(II), Co(II), Fe(II) and Ni(II) (7.5mM) and the ligands 1,10-phenanthroline and 3,4,7,8-tetramethyl-1,10-phenanthroline (7.5mM) all took longer than 30 minutes to kill spermatozoa, *N. gonorrhoea* and *Trep. pallidum*.

When selected chelates of the invention are to be used intravaginally, they are mixed with a carrier which is satisfactory for intravaginal use. Such carriers are well known in the pharmaceutical art. Chelate pessaries (suppositories) which have been used clinically for the treatment of vaginitis generally contain 20 milligrams of the chelate in a 4 gram pessary. Instead of applying the chelate as a pessary it can also be administered in a aerosol foam, jelly, cream or in a foaming tablet suitable for intravaginal use. The concentration of chelate in the pessary approximates to that used in th present in vitro study on human spermatozoa and is some 75 times that used in the in vitro tests with *N. gonorrhoea* and *Trep. pallidum* described herein. Moreover, it should be noted that rapidly-acting chelates by an active chelate should provide satisfactory protection against the contraction of venereal disease during intercourse.

In this specification we have shown test results for only certain chelates of those specified in the invention. However, these results are indicative of the activity of the group and, provided they are not toxic to human tissues, many of the other chelates should also be satisfactory for clinical use although their concentrations may need to be higher than those already considered, and particularly than that of bis(3,4,7,8-tetramethyl-1,10-phenanthroline)copper(II) diacetate which is at present the clinically preferred compound.

The claims defining the invention are as follows:

1. A method of inactivating spermatozoa and killing the microorganisms *Neisseria gonorrhea* and *Treponema pallidum* comprising contacting the same with a pharmaceutically acceptable carrier containing a effective, contraceptive and antivenereal amount of a metal chelate contraceptive and antiveneral agent selected from the group consisting of (M B$_3$) X$_n$   and   (M B$_2$) X$_n$ wherein M represents a metal selected from ferrous (iron(II)), zinc(II), manganous (manganese(II)), cobaltous (cobalt (II)), cobaltic(cobalt(III)), cuprous(copper(I)), cupric(copper(II)), nickelous(nickel(II)), chromous (chromium (II)), chromic (chromium (III)), cadmium(II), ruthenous(ruthenium(II)), osmous(osmium(II)), platinous(platinum(II)), palladous(palladium(II)), rhodic(rhodium (III)) and iridous(iridium-(III)), wherein B represents a ligand provided by a base consisting of 1,10-phenanthroline, 2,2'-bipyridine or their substituted derivatives, the 1,10-phenanthroline base having substituents and mixtures of substituents selected from alkyl, aryl, nitro and chloro in one to eight of the 2-, 3-, 4-, 5-, 6-, 7-, 8-, and 9-, positions and the 2,2'-bipyridine base having substituents selected from alkyl, aryl, nitro and chloro in one to six of the 4-, 5-, 6-, 4'-, 5'-, and 6'- positions, in the case of 1,10-phenanthroline the substitution being in one to eight of the specified positions with the alkyl group and in one or two of the specified positions with the nitro, chloro, aryl, each alkyl substituent of 1 to 16 carbon atoms, the total of all carbon atoms in such substituents not exceeding 16, and where di-substitution involves the 3-, 4-, and 7-, 8-, positions either pairs of carbon atoms may form part of 5-membered and 6-membered cycloalkane ring systems and such aryl, mono- and di-substituents totalling from 4 to 16 carbon atoms, and in the case of the 2,2'-bipyridine there being substitution in one to six of the specified positions with the alkyl groups, and mono-substitution and di-substitution in the 4- and 4'- and 5- and 5'-positions with the nitro, chloro, aryl each alkyl substituent of 1 to 16 carbon atoms, the total of all carbon atoms in such substituents not exceeding 16, and such aryl, totalling from 4 to 16 carbon atoms; wherein X represents the anion of pharmaceutically acceptable inorganic and organic acids; and wherein $n$ represents an integer determined by the oxidation state of the metal.

2. A contraceptive method as claimed in claim 1 wherein the ligand B has six or less substituents in the case of 1,10-phenanthroline bases and four or less in the case of 2,2'-bipyridine bases.

3. A contraceptive method as claimed in claim 1 wherein the ligand B is a tetraalkyl substituted 1,10-phenanthroline.

4. A contraceptive method as claimed in claim 3 wherein the ligand B is a tetramethyl substituted 1,10-phenanthroline.

5. A contraceptive method as claimed in claim 4 wherein the ligand B is selected from the group consisting of 3,4,5,6-$(CH_3)_4$-1,10phenanthroline, 3,4,7,8-$(CH_3)_4$-1,10phenonthroline, and 3,5,6,8-$(CH_3)_4$-1,10phenanthroline.

6. A contraceptive method as clamed in claim 3 wherein the ligand B has two pairs of different alkyl substituents selected from the group consisting of methyl, ethyl, propyl, butyl, amyl and hexyl.

7. A contraceptive method as claimed in claim 1 wherein the ligand B is a dialkyl substituted 1,10-phenanthroline.

8. A contraceptive method as claimed in claim 7 wherein the ligand B is a diemthyl substituted 1,10-phenanthroline.

9. A contraceptive method as claimed in claim 8 wherein the ligand B is selected from the group consisting of 2,9-$(CH_3)_2$-1,10-phenanthroline, 3,4-$(CH_3)_2$-1,10-phenanthroline, 3,8-$(CH_3)_2$-1,10-phenanthroline, 4,5-$(CH_3)_2$-1,10-phenanthroline, 4,7-$(CH_3)_2$-1,10-phenanthroline and 5,6-$(CH_3)_2$-1,10-phenanthroline.

10. A contraceptive method as claimed in claim 1 wherein the ligand is a trimethyl substituted 1,10-phenanthroline.

11. A contraceptive method as claimed in claim 10 wherein the ligand is selected from the group consisting of 3,4,7-$(CH_3)_3$-1,10-phenanthroline and 3,4,8-$(CH_3)_3$-1,10-phenanthroline.

12. A contraceptive method as claimed in claim 1 wherein the ligand B is a hexamethyl substituted 1,10-phenanthroline.

13. A contraceptive method as claimed in claim 1 wherein the ligand B is monosubstituted.

14. A contraceptive method as claimed in claim 13 wherein the substituent is selected from the group consisting of alkyl, aryl, nitro and chloro.

15. A contraceptive method as claimed in claim 14 wherein the alkyl substituent is selected from the group consisting of methyl, ethyl, propyl, butyl, amyl and hexyl.

16. A contraceptive method as claimed in claim 14 wherein the aryl substituent is selected from the group consisting of phenyl, tolyl, and xylyl.

17. A contraceptive method comprising inactivating spermatazoa by contacting the same with an effective contraceptive amount of a copper (I) chelate or copper (II) chelate of mono-alkyl, di-alkyl, tri-alkyl, tetra-alkyl or hexa-alkyl substituted 1,10-phenanthroline.

18. A contraceptive method as claimed in claim 17 wherein the chelate is mono-substituted and the substituent is selected from the group consisting of phenyl, tolyl, xylyl, nitro and chloro.

19. An antivenereal method comprising killing the microorganisms *Neisseria gonorrhea* and *Treponema pallidum* by placing intravaginally an antivenereal effective amount of a transition metal chelate, the ligand of which is a dimethyl substituted 1,10-phenanthroline.

20. An antivenereal method as claimed in claim 19 wherein the ligand is selected from the group consisting of 2,9-$(CH_3)_2$-1,10-phenanthroline, 3,4-$(CH_3)_2$-1,10-phenanthroline, 3,8-$(CH_3)_2$-1,10-phenanthroline, 4,5-$(CH_3)_2$-1,10-phenanthroline, 4,7-$(CH_3)_2$-1,10-phenanthroline and 5,6-$(CH_3)_2$-1,10-phenanthroline.

21. A contraceptive method as claimed in claim 1 wherein the ligand B is a tetra-alkyl substituted 2,2'-bipyridine.

22. A contraceptive method as claimed in claim 21 wherein the substituents are selected from the group consisting of methyl, ethyl, propyl and butyl, amyl and hexyl which may or may not be the same.

23. A contraceptive method as claimed in claim 1 wherein the ligand B is a mono-substituted or di-substituted 2,2'-bipyridine.

24. A contraceptive method as claimed in claim 23 wherein the ligand B is selected from the group consisting of phenyl, tolyl, xylyl, nitro and chloro.

25. A contraceptive method as claimed in claim 21 wherein the chelate is a chelate of copper (I) or copper(II).

26. An antivenereal method comprising killing the microorganisms *Neisseria gonorrhea* and *Treponema pallidum* by placing intravaginally an antivenereal effective amount of a copper (I) chelate and copper (II) chelate, the ligand of which is a mono-alkyl, di-alkyl or tri-alkyl substituted 1,10-phenanthroline, in the case of a mono-alkyl substitution the substituent group being a member selected from the group consisting of methyl, ethyl and propyl, in the case of di-alkyl substitution the two substituent groups are selected from the group consisting of methyl and ethyl, and in the case of tri-alkyl substitution all three groups are methyl.

27. A method of inactivating spermatozoa comprising contacting the same with a pharmaceutically acceptable carrier containing an effective amount of a metal chelate selected from the group consisting of $$(M\ B_2^+)\ X_n\ \text{and}\ (M\ B_3^+)\ X_n$$

wherein M represents a metal selected from cuprous (copper I) and cupric (copper II), wherein B represents a ligand provided by a base consisting of 1,10-phenanthroline, or its substituted derivatives, the 1,10-phenanthroline base having substituents and mixtures of substituents selected from the group consisting of alkyl, aryl, nitro and chloro in one to eight of the 2-, 3-, 4-, 5-, 6-, 7-, 8-, and 9- positions, the substitution being in one to eight of the specified positions with the alkyl group and in one or two of the specified positions with the nitro, chloro, or aryl group, each alkyl substituent comprising 1 to 16 carbon atoms, the total of all carbon atoms in such substituents not exceeding 16, and where di-substitution involves the 3-, 4-, and 7-, 8- positions either pairs of carbon atoms may form part of 5-membered and 6-membered cycloalkane ring systems and such aryl, mono- and di-substituents totalling from 4 to 16 carbon atoms, wherein X represents the anion of pharmaceutically acceptable inorganic and organic acids; and wherein $n$ represents an integer determined by the oxidation state of the metal.

28. A method as claimed in claim 1 wherein the anion X is sulphate in the case of Fe(II) and Ni(II) and acetate in all others.

* * * * *